United States Patent
Gasper

(10) Patent No.: US 10,207,018 B2
(45) Date of Patent: Feb. 19, 2019

(54) LOW WATTAGE USB POWERED WAX WARMERS

(71) Applicant: S.C. Johnson & Son, Inc., Racine, WI (US)

(72) Inventor: Thomas P. Gasper, Germantown, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 403 days.

(21) Appl. No.: 14/722,387

(22) Filed: May 27, 2015

(65) Prior Publication Data
US 2016/0346418 A1    Dec. 1, 2016

(51) Int. Cl.
| | |
|---|---|
| *A61L 9/03* | (2006.01) |
| *H05B 3/12* | (2006.01) |
| *H05B 3/00* | (2006.01) |
| *A61L 9/012* | (2006.01) |

(52) U.S. Cl.
CPC .............. *A61L 9/03* (2013.01); *A61L 9/012* (2013.01); *H05B 3/0014* (2013.01); *H05B 3/12* (2013.01)

(58) Field of Classification Search
None
See application file for complete search history.

(56) References Cited

U.S. PATENT DOCUMENTS

| | | | | |
|---|---|---|---|---|
| 2,685,020 A * | 7/1954 | Laibow | ............... | A01M 1/2077 392/390 |
| 3,784,787 A * | 1/1974 | Shevlin | ............... | A47J 39/006 165/918 |
| 4,575,928 A * | 3/1986 | Starnes | ............... | A47J 27/004 228/179.1 |
| 4,731,522 A * | 3/1988 | Manchester | ........ | A01M 1/2077 219/433 |
| 6,412,670 B1 * | 7/2002 | Randmae | ............... | C11C 5/023 222/452 |
| 6,609,935 B2 | 8/2003 | Huang | | |
| 7,046,919 B2 * | 5/2006 | Shimizu | ............... | A61L 9/03 392/390 |
| 7,133,605 B2 * | 11/2006 | Niemeyer | ............... | A61L 9/03 219/438 |
| 7,252,805 B2 * | 8/2007 | Hart | ............... | A01M 1/2066 122/366 |

(Continued)

FOREIGN PATENT DOCUMENTS

| | | |
|---|---|---|
| CN | 2738806 Y | 11/2005 |
| CN | 202802263 U | 3/2013 |

OTHER PUBLICATIONS

PCT/US2016/033868 International Search Report and Written Opinion dated Jul. 20, 2016.

(Continued)

*Primary Examiner* — Thor Campbell
(74) *Attorney, Agent, or Firm* — Quarles & Brady LLP

(57) ABSTRACT

A wax warmer assembly includes a housing having an outermost edge defining an opening. The housing further includes an annular ridge below the outermost edge. The wax warmer assembly further includes a dish with a peripheral edge, a heater affixed to the dish, and a USB power cord in electrical communication with the heater. Further, the dish is disposed in the opening of the housing and the peripheral edge of the dish engages with the annular ridge of the housing.

20 Claims, 7 Drawing Sheets

(56) References Cited

U.S. PATENT DOCUMENTS

| | | | |
|---|---|---|---|
| 7,329,839 B2* | 2/2008 | Palmer | F21V 35/00 |
| | | | 219/438 |
| 7,402,776 B2 | 7/2008 | Smith | |
| 7,778,531 B2 | 8/2010 | Cheung | |
| 8,032,014 B2 | 10/2011 | Cheung | |
| 8,364,028 B1* | 1/2013 | Vaske | A61L 9/03 |
| | | | 219/385 |
| 8,625,977 B2 | 1/2014 | Cheung | |
| 8,787,739 B2 | 7/2014 | Hsiao | |
| 8,809,744 B2 | 8/2014 | Stewart | |
| 2003/0087554 A1 | 5/2003 | Huang | |
| 2004/0149733 A1 | 8/2004 | Abbott et al. | |
| 2005/0016985 A1* | 1/2005 | Haas | A61L 9/03 |
| | | | 219/438 |
| 2005/0169666 A1* | 8/2005 | Porchia | A01M 1/02 |
| | | | 399/111 |
| 2006/0163240 A1 | 7/2006 | Xiao | |
| 2006/0219694 A1* | 10/2006 | Wu | A61L 9/03 |
| | | | 219/400 |
| 2006/0258215 A1 | 11/2006 | Lai et al. | |
| 2007/0031298 A1* | 2/2007 | Roumpos | A61L 9/02 |
| | | | 422/125 |
| 2009/0004614 A1* | 1/2009 | Furner | A61L 9/03 |
| | | | 431/291 |
| 2009/0148142 A1 | 6/2009 | McGee et al. | |
| 2010/0096376 A1* | 4/2010 | Hsiao | A61L 9/03 |
| | | | 219/201 |
| 2010/0270943 A1* | 10/2010 | Cook | A61L 9/03 |
| | | | 315/291 |
| 2011/0110072 A1* | 5/2011 | Hsiao | A61L 9/03 |
| | | | 362/96 |
| 2011/0110824 A1* | 5/2011 | Hsiao | A61L 9/035 |
| | | | 422/125 |
| 2011/0284522 A1 | 11/2011 | Hsieh et al. | |
| 2012/0024837 A1* | 2/2012 | Thompson | A61L 9/03 |
| | | | 219/433 |
| 2012/0183280 A1* | 7/2012 | Kowalec | A61L 9/03 |
| | | | 392/386 |
| 2012/0298770 A1 | 11/2012 | Cheung | |
| 2012/0318779 A1* | 12/2012 | Juarez | H01R 33/22 |
| | | | 219/209 |
| 2013/0020307 A1* | 1/2013 | Ashton | H05B 3/68 |
| | | | 219/387 |
| 2013/0170184 A1* | 7/2013 | Browder | A61L 9/015 |
| | | | 362/96 |
| 2014/0126892 A1 | 5/2014 | Hsiao | |
| 2014/0268652 A1 | 9/2014 | Li | |
| 2014/0286024 A1 | 9/2014 | Li | |
| 2015/0174278 A1* | 6/2015 | Belongia | A61L 9/03 |
| | | | 392/386 |
| 2015/0283280 A1* | 10/2015 | Belongia | A61L 9/03 |
| | | | 392/386 |
| 2015/0305089 A1* | 10/2015 | Belongia | H05B 3/0052 |
| | | | 219/438 |

OTHER PUBLICATIONS

International Search Report and Written Opinion dated Aug. 23, 2017, International Application No. PCT/US2017/035189, 10 pages.

* cited by examiner

LOW WATTAGE USB POWERED WAX WARMERS

CROSS REFERENCE TO RELATED APPLICATIONS

Not applicable

REFERENCE REGARDING FEDERALLY SPONSORED RESEARCH OR DEVELOPMENT

Not applicable

SEQUENTIAL LISTING

Not applicable

BACKGROUND

Field of the Disclosure

The present disclosure generally relates to a wax warmer, and more specifically, to a low wattage warmer powered by a USB power cord for use with a wax melt to dispense materials into the surrounding environment.

Description of the Background of the Disclosure

Traditional electric wax warmers are known to provide similar benefits as conventional candles through the provision of a pleasant aroma and/or illumination to the surrounding atmosphere or environment. These wax warmers have a heater in indirect thermal contact with a reservoir for holding a wax melt or infused oil, which, when heated, provide a pleasant aroma. In most electric wax warmers, the heater is mounted to a metal plate, which the reservoir rests on, for better dispersion of heat to the reservoir holding the wax melt. The wax warmers are typically powered by plugging traditional AC power plugs into wall outlets.

A common drawback to these prior art electric wax warmers is that the warmers use over 20 watts of power to fully melt the wax in about 40 to about 60 minutes due to the limitation of the indirect thermal contact of the heater to the reservoir. Also, not all household outlets deliver a consistent voltage level and some places in the world require different plug adaptors.

There is therefore a need for a more universal wax warmer that uses a lower amount of power than traditional wax warmers, while maintaining the same time to melt the wax. The present disclosure provides for such a low powered wax warmer with a heater in direct contact with a reservoir. The assembly described in the present disclosure can melt the wax in the same amount of time as traditional AC powered wax warmers as well as use fewer components, which makes the end product more affordable to users.

SUMMARY

According to one aspect, a wax warmer assembly includes a housing having an outermost edge defining an opening. The housing further includes an annular ridge below the outermost edge. The wax warmer assembly further includes a dish with a peripheral edge, a heater affixed to the dish, and a USB power cord in electrical communication with the heater. Further, the dish is disposed in the opening of the housing and the peripheral edge of the dish engages with the annular ridge of the housing.

According to another aspect, a wax warmer assembly includes a housing having an opening, a plate disposed in the opening of the housing for directly receiving a wax melt, a heater directly affixed to the plate, and a USB power cord in electrical communication with the heater. Further, a total power input of the wax warmer assembly is at most 10 watts.

According to a different aspect, a wax warmer assembly includes a housing, a dish having a bottom surface with a bottom surface area, a heater affixed to the bottom surface of the plate defining a contact area, and a USB power cord. Further, the contact area is about 1% to about 64% of the bottom surface area of the plate.

DETAILED DESCRIPTION OF THE DRAWINGS

Figure 1:
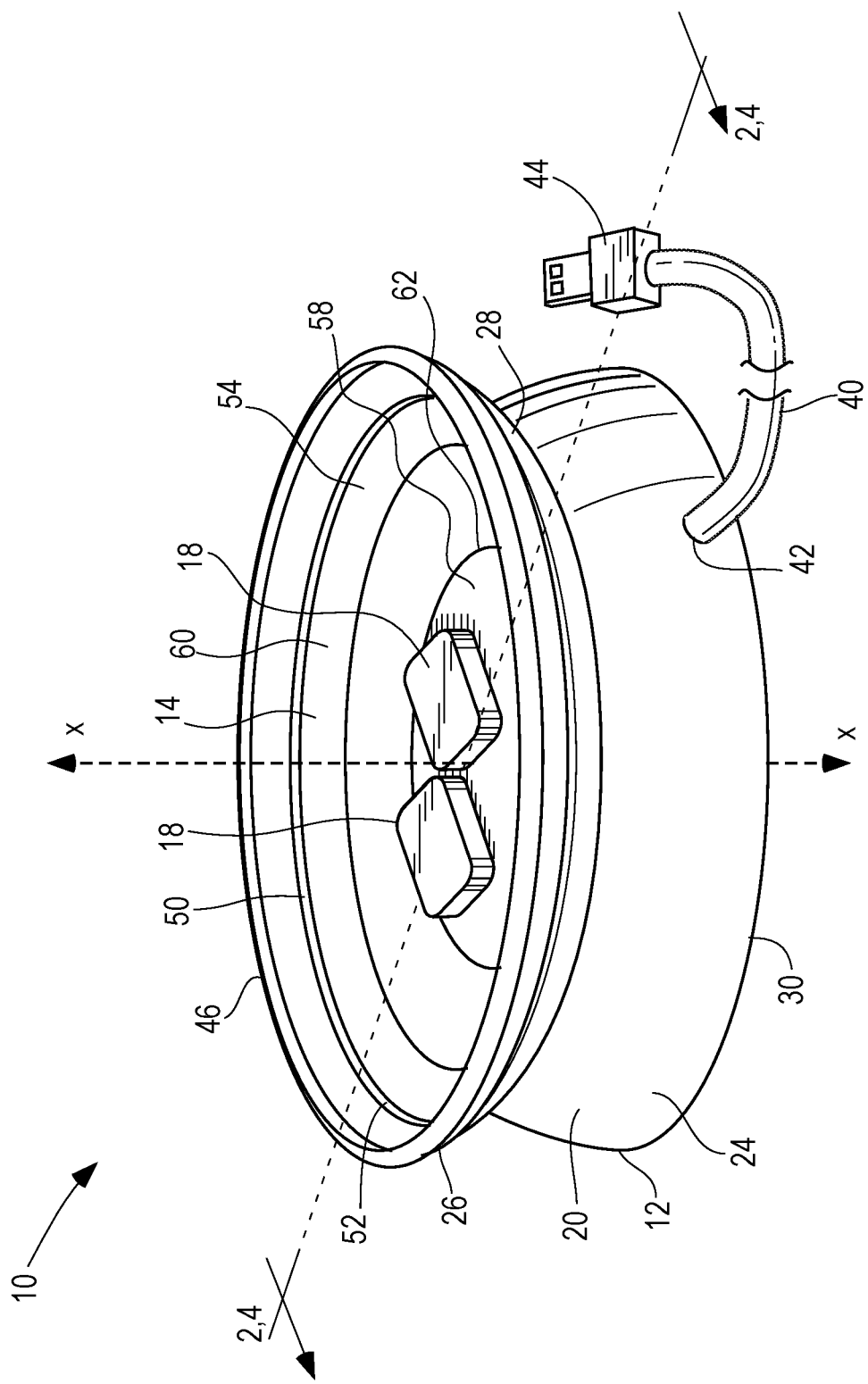
FIG. 1 is an isometric view of a wax warmer assembly including a dish.
Figure 2:
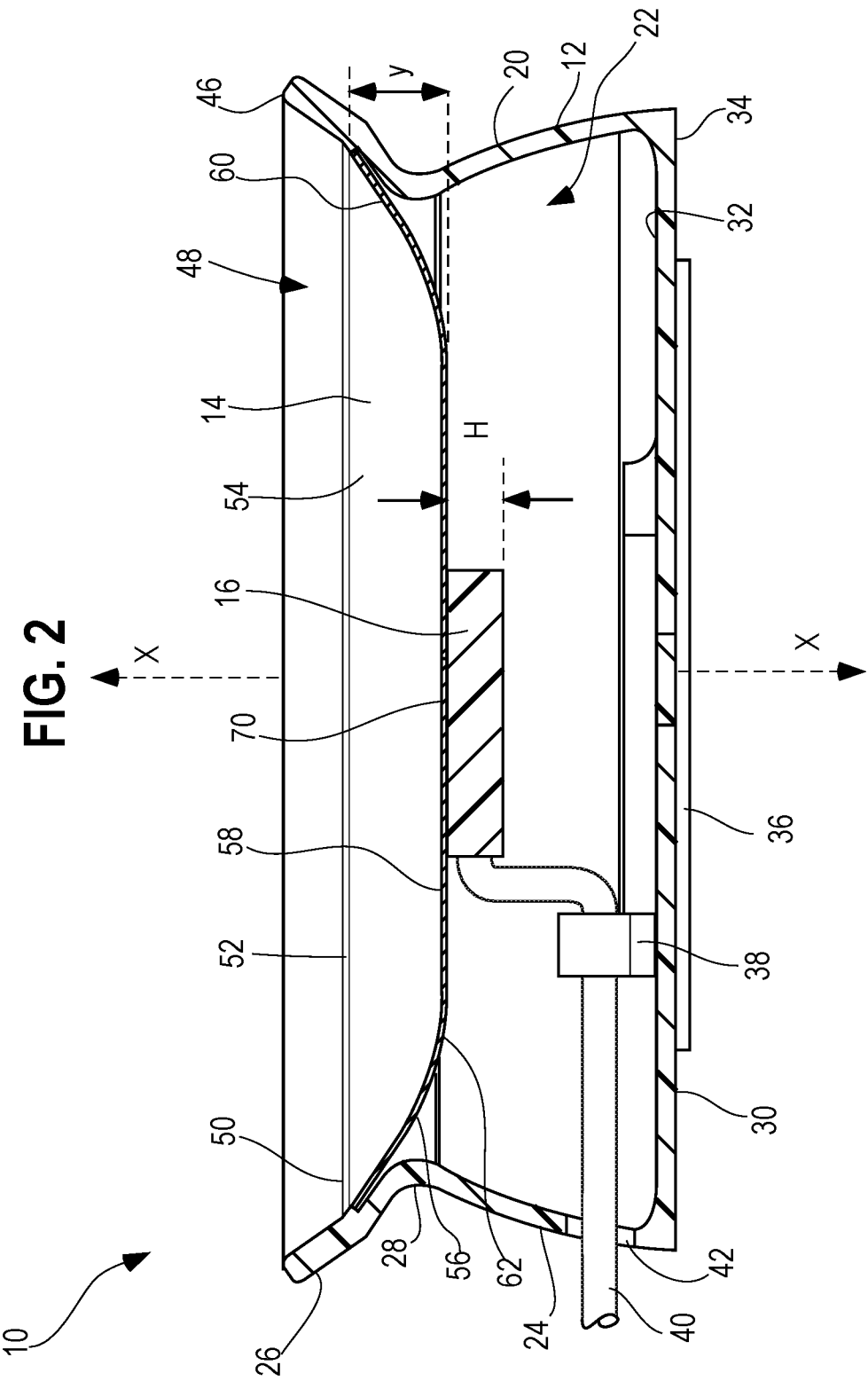
FIG. 2 is a cross-sectional view of the wax warmer assembly taken generally along the lines 2-2 of FIG. 1 with a wax melt removed for purposes of clarity.
Figure 3:
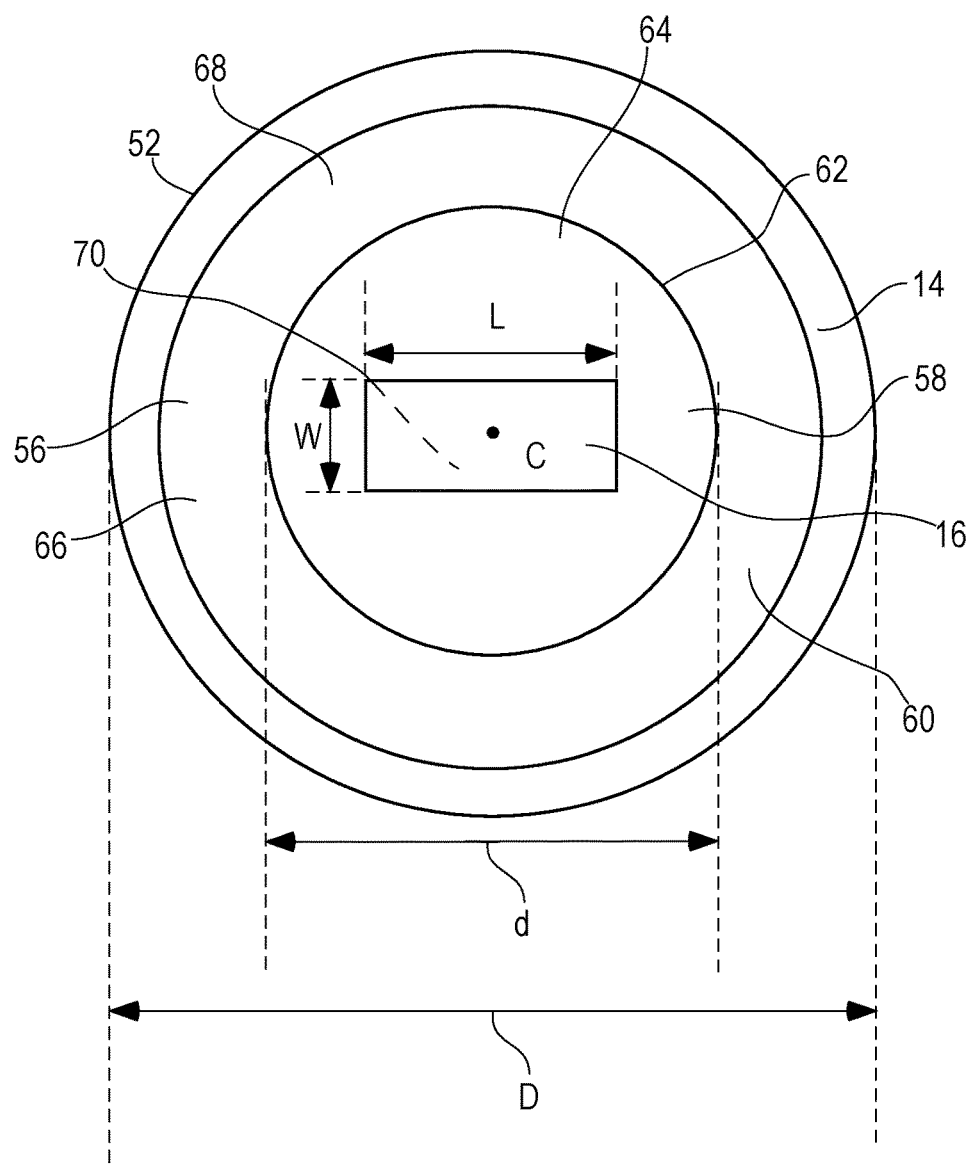
FIG. 3 is a bottom plan view of just the dish of the wax warmer assembly of FIG. 1.

FIGS. 1-3 generally depict a wax warmer assembly 10. The wax warmer assembly 10 includes a housing 12, a dish or a plate 14, and a heater 16. The housing 12 is fashioned to house the heater 16 and retain the dish 14. The wax warmer assembly 10 is designed to heat at least one wax melt 18 and thereby release a fragrance or other volatile material contained therein into the surrounding environment.

The wax melt 18 is wickless and may comprise any geometric shape. In some embodiments, the wax melt 18 has a generally square shape with a slightly rounded curvature imparted thereto at an area where sidewalls of the wax melt 18 intersect with each other. It is contemplated that the shape of the wax melt 18 may be configured to be beneficial for manufacturing purposes or aesthetic reasons or both. Each wax melt 18 weighs between about 0.005 kg to about 0.04 kg. In one embodiment, each wax melt 18 weighs more than about 0.01 kg and less than about 0.03 kg. In another embodiment, each wax melt 18 weighs more than about 0.01 kg. In an additional embodiment, each wax melt 18 is about 0.011 kg.

Referring to FIGS. 1 and 2, the hollow housing 12 includes a sidewall 20 defining an inner space 22 (see FIG. 2). The sidewall 20 includes a bottom portion 24 and a top portion 26 separated by a narrowed waist portion 28. In the present embodiment the bottom portion 24 and the top portion 26 of the housing 12 are substantially bowl shaped and generally circular, when viewed from the top. It has been contemplated that the housing 12 may take any geometric shape, e.g., a square or an octagon, to provide different appearances. In the present embodiment the housing 12 is made of polypropylene. It has been contemplated that other thermoplastic polymers may be used as well as other materials known to those having ordinary skill in the art, such a as ceramic, plastic, metal, stone, or other natural material. Further, the exterior surfaces of the housing 12 may be provided with any type of surface indicia, raised patterns, or any other decorations to configure the wax warmer assembly 10 for aesthetic purposes.

Still referring to FIGS. 1 and 2, the bottom portion 24 of the sidewall 20 includes a base 30 having an interior surface 32, which faces the interior space 22 of the housing 12, and an exterior surface 34 for resting on a horizontal surface such as a table or a desk. In the present embodiment the exterior surface 34 of the base 30 includes a nonslip pad 36 to provide stability to the wax warmer assembly 10. In other examples the base may include extensions (e.g., feet) or other elements with high coefficients of friction generally known to those having ordinary skill in the art. The interior surface 32 of the base 30 may include a cord guiding structure 38 for guiding an electrical cord 40 from the heater 16 to a cord aperture 42 provided in the bottom portion 24 of the sidewall 20 proximal to the base 30. In one embodiment the cord guiding structure 38 may form an upside-down "U" shape extending up from the interior surface 32 of the base 30 into the interior space 22 of the housing. The cord guiding structure 38 may be any shape capable of holding the electrical cord 40, such as square shaped or circular shaped. In other embodiments two or more cord guiding structures 38 may be provided on the interior surface 32 of the base 30 to provide more guidance to the electrical cord 40.

With reference to FIG. 1, the cord aperture 42 is provided in the bottom portion 24 of the sidewall 20 proximal to the base 30. The cord aperture 42 provides a pass-through for the electrical cord 40 from the inner space 22 of the housing 12 to the space outside of the wax warmer assembly 10. In the present embodiment the electrical cord 40 is a USB power cord with a corresponding USB plug 44 at an end of the cord 40 for plugging into an adaptor (not shown) or an electronic device such as a computer (not shown). The electrical cord 40 is shown with a break in its length to depict that the electrical cord 40 can be any length. In one embodiment the electrical cord 40 may be about 4 feet long. In another embodiment the electrical cord 40 may be about 2 feet to about 10 feet long. The USB electrical cord 40 is DC powered via USB and delivers a total power input of about 3 watts to about 10 watts. In another embodiment the electrical cord may deliver a total power input of about 7 watts. Other types of plugs have been contemplated as well. In one embodiment the electrical cord 40 may connect to the heater 16 with a micro USB plug (not shown) adapted to mate with a socket (not shown) on the heater 16. In other embodiments the electrical cord 40 may be permanently attached to the heater 16. Another alternative embodiment may include batteries (not shown) to provide electrical power to the heater 16.

Turning again to FIGS. 1 and 2, the top portion 26 of the sidewall 20 of the housing 12 is generally bowl shaped and has an outermost edge 46, which defines a first opening 48 for receiving the dish 14. The top portion 26 of the sidewall 20 may include a protruding annular ridge 50 for permanently engaging with a peripheral edge 52 of the dish 14. In the present embodiment, the peripheral edge 52 of the dish 14 is located at a position below the outermost edge 46 of the top portion 26 of the sidewall 20, along a longitudinal axis X. Therefore, the peripheral edge 52 of the dish 14 is not coextensive with the outermost edge 46 of the top portion 26 of the sidewall 20. Also, in the present embodiment, the peripheral edge 52 of the dish 14 snap fits with the annular ridge 50 of the top portion 26 of the sidewall 20. Other methods of permanently engaging the peripheral edge 52 of the dish 14 with the annular ridge 50 of the top portion 26 of the sidewall 20 have been contemplated, such as crimping, ultrasonic welding, overmolding, and use of an adhesive. Further, a sealant may be coated on the peripheral edge 52 of the dish 14 prior to engaging with the annular ridge 50, such as an RTV sealant to prevent any melted wax melt 18 from seeping into the inner space 22 of the housing 12. It has also been contemplated that the top portion 26 of the sidewall 20 may not include a protruding annular ridge 50. Instead, the peripheral edge 52 of the dish 14 may simply rest within the top portion 26 of the sidewall 20 and the sealant may be coated on the peripheral edge 52 of the dish 14 to prevent melted wax melt 18 from seeping into the inner space 22 of the housing 12.

As seen best in FIG. 2, the dish 14 includes a top surface 54 for receiving at least one wax melt 18 and a bottom surface 56 for receiving the heater 16. The dish 14 includes a center portion 58 and a sidewall portion 60. In the current embodiment, the center portion 58 is substantially flat and the sidewall portion 60 is curvilinear. The sidewall portion 60 extends from an inflection point at a peripheral edge 62 of the flat center portion 58 to the peripheral edge 52 of the dish 14 to define a depth Y about the longitudinal axis X. In the current embodiment the depth Y of the dish 14 is about 12 mm. In other examples, the depth Y of the dish is about 0 mm to about 25 mm.

As best seen in FIG. 3, the dish 14 has a major diameter D, which is defined by a circle created by the peripheral edge 52 of the dish 14, and a minor diameter d, which is defined by the peripheral edge 62 of the flat center portion 58. In the present embodiment the major diameter D is about 82 mm and the minor diameter is about 54 mm. In other examples, the major diameter D of the dish 14 is about 20 mm to about 90 mm and the minor diameter d of the dish 14 is about 0 mm to about 90 mm. In the present embodiment the ratio of the major diameter D to the minor diameter d is about 3:2. In other embodiments the ratio can be larger than 3:2, which would result in a dish 14 having a more continually curved shape and a smaller flat center portion 58. In yet another embodiment, the dish 14 may have a continually curvilinear sidewall portion 60 and no flat center portion 58, in which the ratio of the major diameter D to the minor diameter d is essentially non-existent because there is no minor diameter d. In a different embodiment the ratio may be smaller than 3:2, which would result in a dish 14 with a larger flat center portion 58. In one alternative embodiment, the dish 14 is a plate having no sidewall portion 60. The plate is substantially planar and only comprises a flat center portion 58 for receiving the wax melt 18. In this embodiment the plate engages with the annular ridge 50 of the top portion 26 of the sidewall 12 and creates a bowl-like reservoir for the wax melts 18.

Referring to FIGS. 2 and 3, in the present embodiment the center portion 58 has a surface area 64 of about 2290 mm$^2$ and the sidewall portion 60 has a surface area 66 of about 2560 mm$^2$. In other examples the surface area 64 of the center portion 58 is about 0 mm to about 6358.5 mm$^2$ and the surface area 66 of the sidewall portion 60 is about 0 to 8321 mm$^2$. The total surface area 68 of the bottom surface 56 of the dish 14 is calculated by adding the surface area 64 of the center portion 58 to the surface area 66 of the sidewall portion 60. In the present embodiment the total surface area 68 of the bottom surface 56 of the dish 14 is about 4850 mm$^2$. In other examples, the total surface area 68 of the bottom surface 56 of the dish 14 is about 314 mm$^2$ to about 8,321 mm2.

Further, in the present embodiment the dish 14 is made from aluminum. However, any other thermally conductive material as known to those having ordinary skill in the art may be used, such as, copper, steel, carbon impregnated plastics, or thermally conductive polymers.

Referring still to FIGS. 2 and 3, the heater 16 is directly affixed to the bottom surface 56 of the dish 14 by means of an adhesive, such as a self adhesive polyester film or a thermally conductive epoxy, which is coated on the heater 16. The heater 16 is directly affixed to the bottom surface 56 of the dish 14 in a manner that omits any intervening mounting structure to affix the heater 16 to the bottom surface 56 of the dish 14. The heater 16 is directly affixed to the dish 14 by means of an adhesive/glue/tacky substance. The heater 16 may be placed near the center of the dish 14 for an even dispersion of heat over the dish 14. In other embodiments the heater may be placed anywhere on the bottom surface 56 of the dish 14. The heater 16 may be a resistive type heater or may be any other type of heater known to one of ordinary skill. For example, the heater may be a positive thermal coefficient heater, an inductive type heater, or a NiChrome stamped polyester heater. In other examples the heater 16 may be replaced by a series of heaters or any known heating arrangement that allows the heater 16 to make sufficient thermal contact with the dish 14.

Still referring to FIGS. 2 and 3, in the current embodiment the heater 16 is a resistive heater in the form of a ceramic block. In the present embodiment the heater 16 has an electrical resistance of about 3.6 ohms. In other embodiments the heater 16 may have an electrical resistance of about 2.7 ohms to about 6.8 ohms. The ceramic block heater 16 is directly affixed to the bottom surface 56 of the dish 14 with a thermally conductive epoxy. The ceramic block heater 16 is a rectangular prism with a length L of about 20 mm, a width W of about 10 mm, and a height H of about 10 mm. In other examples, the length L of the ceramic block heater 16 is about 12 mm to about 29 mm, the width W of the ceramic block heater 16 is about 6.8 mm to about 27 mm, and the height is about 6.8 mm to about 27 mm.

With specific reference to FIG. 3, a bottom view of the dish 14 is shown with the heater 16 provided thereon. In the present embodiment a contact area 70 between the heater 16 and the center portion 58 of the dish 14 is provided over a center point C of the dish 14. In fact, a center of the heater 16 is aligned with the center point C. Further, the contact area 70 may best be defined as the surface area of the length L and width W of the heater 16, as both the heater 16 and the center portion 58 are flat and juxtaposed with one another. In the illustrated embodiment the contact area 70 is about 200 mm$^2$. In other examples the contact area 70 is about 81.6 mm$^2$ to about 783 mm$^2$. In the current embodiment, the contact area 70 is about 9% of the surface area 64 of the center portion 58 of the dish 14. In other embodiments the contact area 70 may be about 1% to about 64% of the surface area 64 of the center portion 58 of the dish 14. In the illustrated embodiment the contact area 70 is about 4% of the total surface area 68 of the bottom surface 56 of the dish 14. In other embodiments the contact area 70 may be about 1% to about 64% of the total surface area 68 of the bottom surface 56 of the dish 14.

Figure 4:
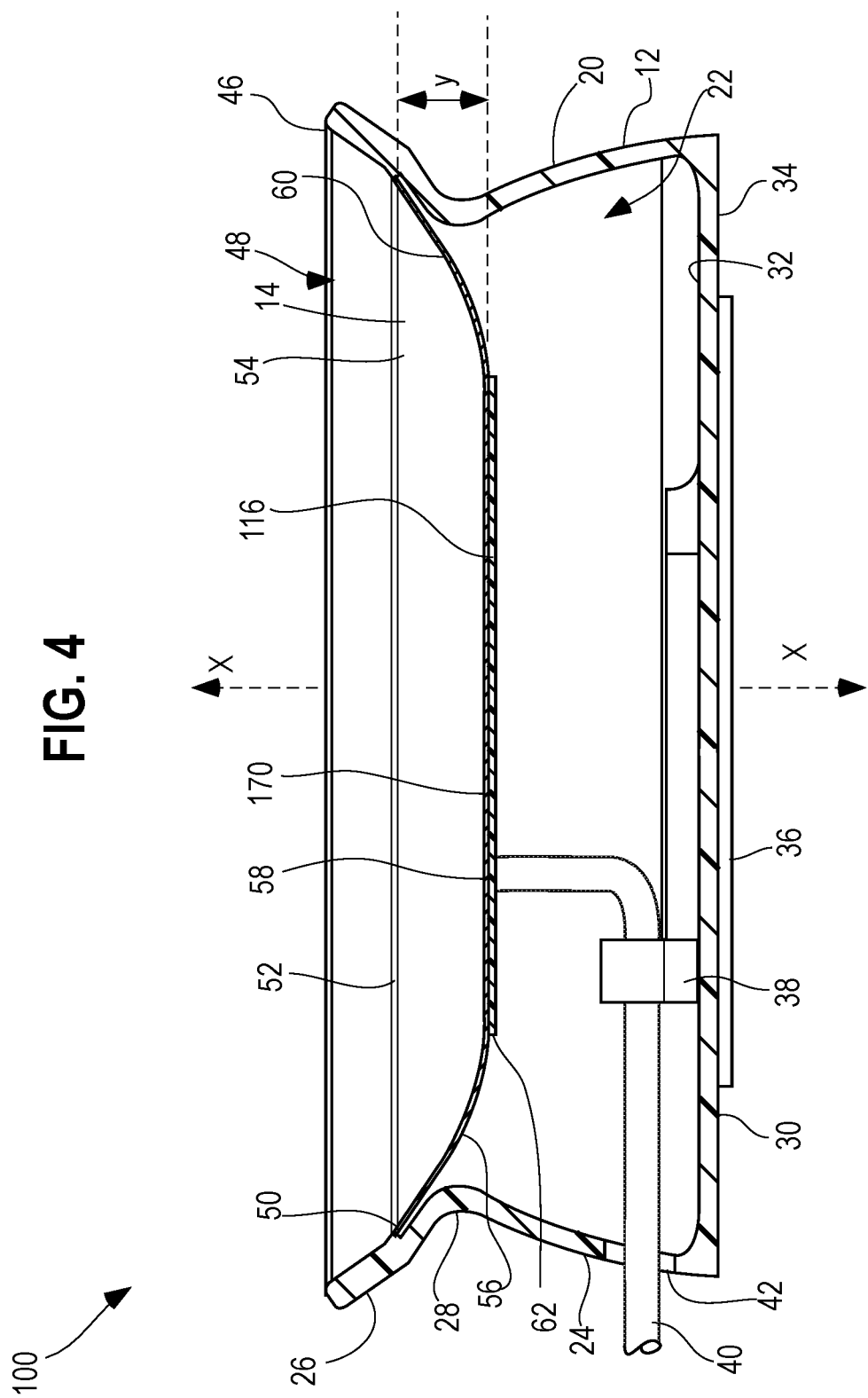
FIG. 4 is a cross-sectional view of another embodiment of the wax warmer assembly taken generally along the lines of 4-4 of FIG. 1 with a wax melt removed for purposes of clarity.
Figure 5:
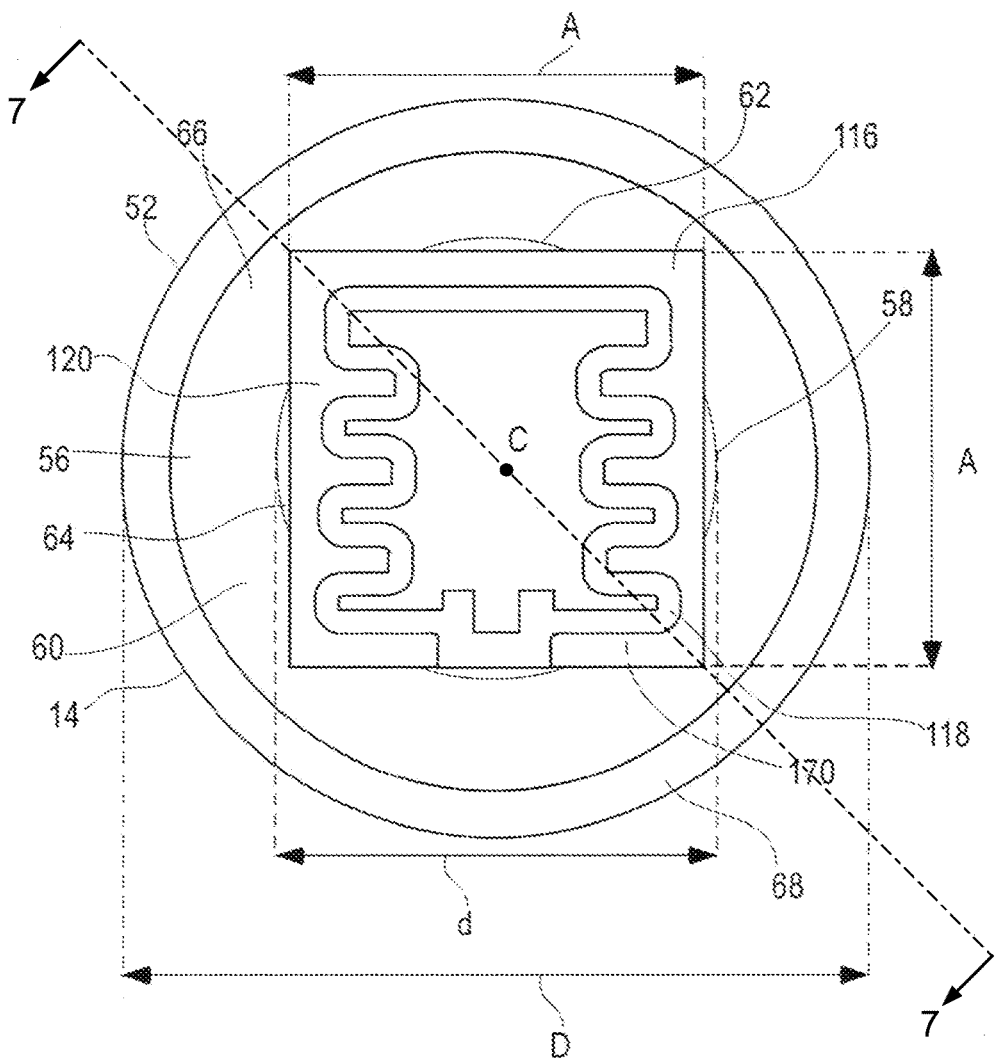
FIG. 5 is a bottom plan view of just the dish of the wax warmer assembly of FIG. 4.
Figure 7:
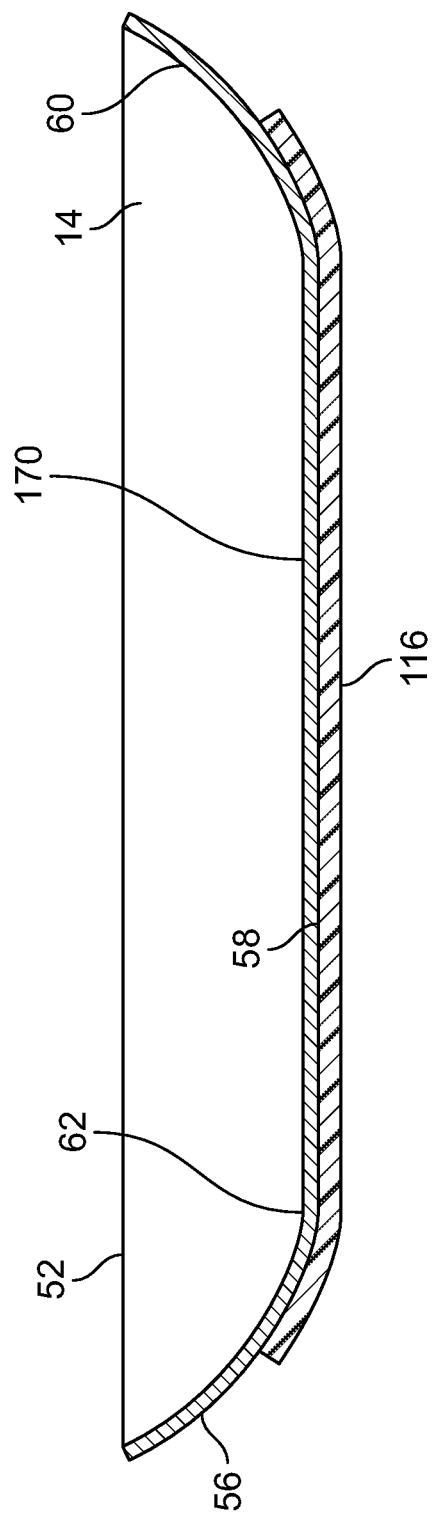
FIG. 7 is a cross-sectional view of the dish and heater of the wax warmer assembly of FIG. 4 taken generally along the line 7-7 of FIG. 5.

FIGS. 4 and 5 depict a wax warmer assembly 100 similar to that shown in FIGS. 1-3 wherein similar structure is provided with identical reference numbers. In the present embodiment a NiChrome stamped polyester heater 116 is used to heat the wax warmer assembly 100. The heater 116 includes a resistive component 118 stamped in a film 120. In the current embodiment the resistive component 118 is a NiChrome plate, however, other resistive metals known to those of skill in the art may be used as well. In the illustrated embodiment the heater 116 has an electrical resistance of about 3.8 ohms. In other embodiments the heater 116 may have an electrical resistance of about 2.3 ohms to about 6.5 ohms. The film 120 is a self adhesive polyester film that directly affixes the heater 116 to the bottom surface 56 of the dish 14. The heater 116 is able to affix to both the flat center portion 58 of the dish 14 as well as the curved sidewall portion 60 of the dish. (See FIG. 7.) In other embodiments, when the dish 14 does not include a flat center portion 58, the heater 116 is able to directly affix to the dish 14 having a continually curved bottom surface 56. In other embodiments a different type of film may be used. In the current embodiment the stamped heater 116 is generally a thin square shape with both sides A being about 50 mm. In other embodiments the sides A of the stamped heater 116 are about 20 mm. It has been contemplated that other shapes may be used for the stamped heater 116 such as round, triangle, hexagon, or any other shape.

With specific reference to FIG. 5, a bottom view of the dish 14 is shown with the heater 116 provided thereon. In the present embodiment a contact area 170 between the heater 116 and the center portion 58 of the dish 14 is provided over the center point C of the dish 14. In fact, a center of the heater 116 is aligned with the center point C. Further, the contact area 170 may best be defined as the surface area of the square stamped heater 116, as both the heater 116 and the center portion 58 are juxtaposed with one another. Therefore, in the current embodiment the contact area 170 is the length of the sides A squared, which is about 2500 mm$^2$. In other embodiments the contact area 170 may be about 400 mm$^2$. In the current embodiment, the contact area 170 is about 109% of the surface area 64 of the flat center portion 58 of the dish 14. In other embodiments the contact area 170 may be about 5% to about 125% of the surface area 64 of the flat center portion 58 of the dish 14, or about 10% to about 100% of the surface area 64, or about 6% to about 64% of the surface area 64. In the current embodiment the contact area 170 is about 52% of the total surface area 68 of the bottom surface 56 of the dish 14. In other embodiments the contact area 170 may be about 1% to about 100% of the total surface area 68 of the bottom surface 56 of the dish 14, or about 2% to about 75% of the total surface area 68, or about 4% to about 64% of the total surface area 68.

The present disclosure allows a user to volatize an active through the use of a power efficient wax warmer assembly that includes fewer components than prior art wax warmers while melting the wax in the same amount of time. Specifically, the wax warmer assembly 10, 100 uses a USB power cord 40 that has a total power input of about 7 watts of power. The total power input of the wax warmer assembly 10, 100 is at most 10 watts. Many prior art wax warmers require about 20 watts of power to operate.

In a specific example, the wax warmer assembly 10 includes a polypropylene housing 12, an aluminum dish 14, a ceramic block heater 16, and a USB electrical cord 40 that receives power from a power source. In this example, two wax melts 18 weighing about 0.011 kg each are placed directly in the aluminum dish 14 and are warmed by the heater 16 directly affixed to the dish 14. The total power input delivered to the heater 16 from the USB electrical cord 40 is about 7 watts. The two wax melts 18 take about 45 minutes to completely liquefy. At this time, the aluminum dish 14 reaches a temperature of about 75 degrees Celsius. After an hour of operation, the maximum temperature of the liquefied wax melts 18 is about 68 degrees Celsius. These same results were achieved by using the stamped NiChrome heater 116 in the wax warmer assembly 100.

Further, the wax warmer assembly 10, 100 of the present disclosure includes four main components: a housing 12, a dish 14 for holding wax melts 18, a heater 16, 116 directly affixed to the dish 14, and an electrical cord 40. On the other hand, many prior art wax warmers include a separate reservoir for holding the wax melts that are placed on a metal plate. Many prior art wax warmers also utilize an intervening mounting structure to affix a heater to a bottom surface of a metal plate, thereby indirectly affixing the heater to the metal plate.

Figure 6:
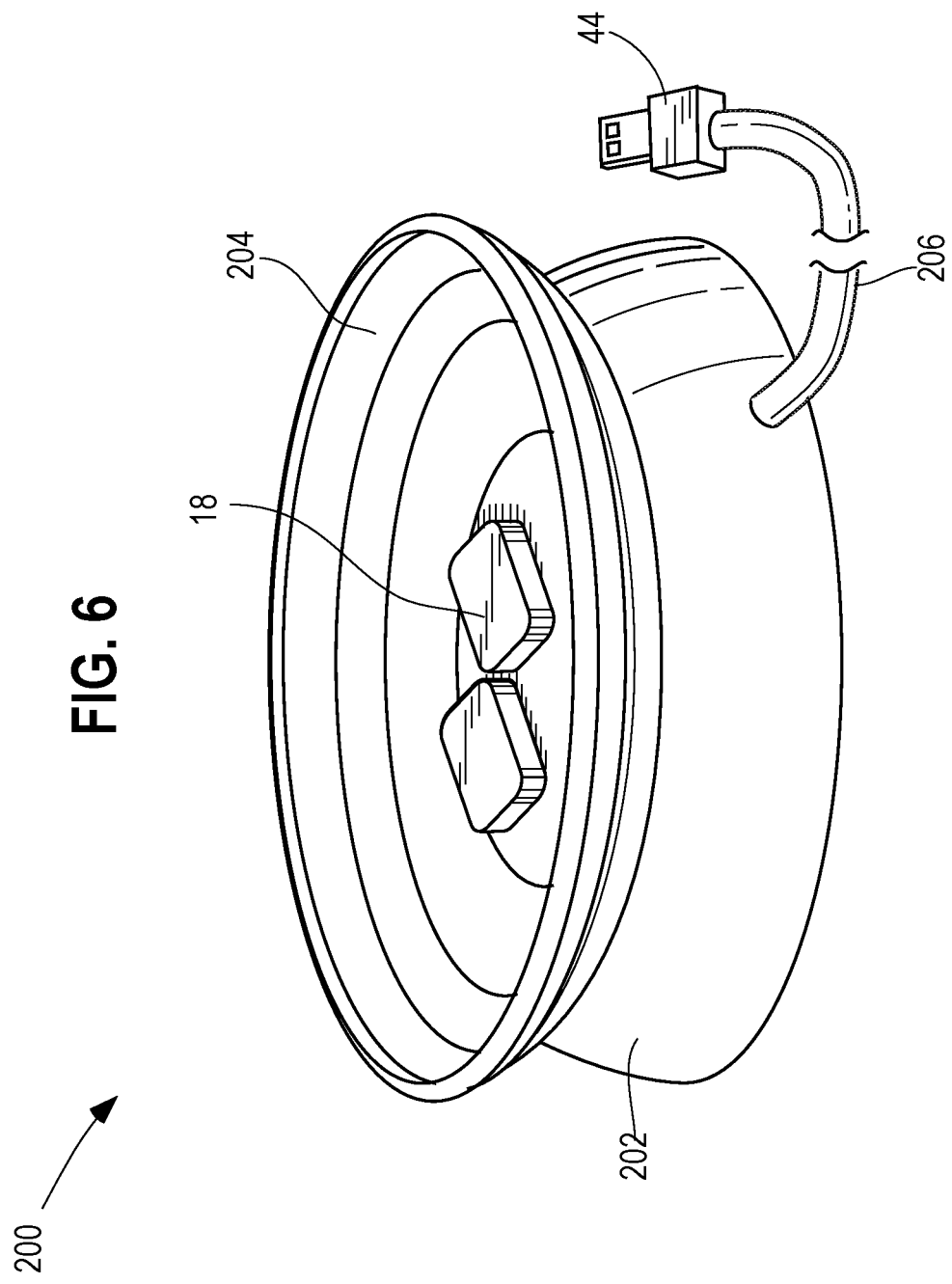
FIG. 6 is an alternative embodiment of the wax warmer assembly of FIG. 1.

Even further, it has been contemplated that a wax warmer assembly 10, 100 may include fewer than four components. As seen in FIG. 6, a wax warmer assembly 200 includes a housing 202 with a bowl like recessed portion 204. A heater similar to the stamped heater 116 is directly attached to a bottom surface defining a lower end of the recessed portion 204 of the housing 202 (not shown). The heater is in electrical communication with an electrical cord 206. In this embodiment, the housing 202 is a single component made by ejection molding of polypropylene material and does not require a separate aluminum dish for holding the wax melts 18, as previously described. Therefore, the wax warmer assembly 200 includes three main components: a housing 202 having a recessed portion 204, a heater 116, and a cord 206.

The exemplary embodiments disclosed herein are not intended to be exhaustive or to unnecessarily limit the scope of the invention. The exemplary embodiments were chosen and described in order to explain the principles of the present invention so that others skilled in the art may practice the invention. As will be apparent to one skilled in the art, various modifications can be made within the scope of the aforesaid description. Such modifications being within the ability of one skilled in the art form a part of the present invention and are embraced by the appended claims.

Other embodiments of the disclosure including all the possible different and various combinations of the individual features of each of the foregoing described embodiments and examples are specifically included herein.

INDUSTRIAL APPLICABILITY

Numerous modifications to the present invention will be apparent to those skilled in the art of wax warmers in view of the foregoing description. Accordingly, this description is to be construed as illustrative only and is presented for the purpose of enabling those skilled in the art to make and use the invention. The exclusive rights to all modifications which come within the scope of the appended claims are reserved.

I claim:

1. A wax warmer assembly, comprising:
a housing including an outermost edge defining an opening and an annular ridge below the outermost edge;
a dish with a peripheral edge, the dish including a flat center portion and a curved sidewall portion, the peripheral edge defining an upper end of the curved sidewall portion;
a heater affixed to the dish; and
a USB power cord in electrical communication with the heater,
wherein the dish is disposed in the opening of the housing, and
wherein the peripheral edge of the dish engages with the annular ridge of the housing.

2. The wax warmer assembly of claim 1, wherein the dish is a metal dish.

3. The wax warmer assembly of claim 2, wherein the heater is affixed to the dish by means of an adhesive.

4. The wax warmer assembly of claim 3, wherein the heater includes a self adhesive film.

5. The wax warmer assembly of claim 3, wherein the adhesive is a thermally conductive epoxy.

6. The wax warmer assembly of claim 1, wherein the wax warmer assembly further comprises a wax melt for emitting a volatile material when heated on the dish.

7. The wax warmer assembly of claim 1, wherein the heater may be a stamped heater or a resistive ceramic block heater.

8. A wax warmer assembly, comprising:
a housing including an opening;
a plate disposed in the opening of the housing for directly receiving a wax melt;
a heater directly affixed to the plate; and
a USB power cord in electrical communication with the heater,
wherein a total power input of the wax warmer assembly provided by the USB power cord is between 7 and 10 watts.

9. The wax warmer assembly of claim 8, wherein the heater is a stamped heater or a resistive ceramic block heater.

10. The wax warmer assembly of claim 9, wherein the USB power cord provides a maximum 5 volt supply to the heater.

11. The wax warmer assembly of claim 10, wherein the plate reaches a maximum temperature of about 75° C.

12. The wax warmer assembly of claim 10, wherein the wax warmer assembly further includes a wax melt with a weight of about 0.011 kg that is placed on the plate.

13. The wax warmer assembly of claim 12, wherein the wax melt has a melting time of about 45 minutes.

14. The wax warmer assembly of claim 13, wherein the wax melt reaches a maximum temperature of about 68° C.

15. A wax warmer assembly, comprising:
a housing;
a dish including a bottom surface with a bottom surface area, the bottom surface including a flat center portion and a curved sidewall portion;
a heater affixed to the bottom surface of the dish defining a contact area, wherein the contact area includes both the flat center portion and at least a portion of the curved sidewall portion of the bottom surface; and
a USB power cord,
wherein the contact area is about 4% to about 64% of the bottom surface area of the dish.

16. The wax warmer assembly of claim 15, wherein the flat center portion has a surface area and the curved sidewall portion has a different surface area.

17. The wax warmer assembly of claim 16, wherein the contact area is about 5% to about 125% of the surface area of the flat center portion.

18. The wax warmer assembly of claim 15, wherein the heater is directly affixed to the dish by means of an adhesive.

19. The wax warmer assembly of claim 15, wherein the heater is a stamped heater or a resistive ceramic block heater.

20. The wax warmer assembly of claim 15 further including a wax melt for emitting a volatile active when in contact with the dish.

* * * * *